(12) United States Patent
Park et al.

(10) Patent No.: US 7,141,589 B2
(45) Date of Patent: Nov. 28, 2006

(54) METHODS OF INHIBITING FORMATION OF VASCULAR CHANNELS AND METHODS OF INHIBITING PROLIFERATION

(75) Inventors: Myung Hee Park, Potomac, MD (US); Paul M Clement, Bethesda, MD (US); Hartmut M Hanauske-Abel, Edgewater, NJ (US); Edith C. Wolff, Bethesda, MD (US); Hynda K Kleinman, Kensington, MD (US); Bernadette M Cracchiolo, Edgewater, NJ (US)

(73) Assignees: The United States of America as represented by the Department of Health and Human Services, Washington, DC (US); University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 10/486,671

(22) PCT Filed: Aug. 23, 2002

(86) PCT No.: PCT/US02/26909

§ 371 (c)(1),
(2), (4) Date: May 11, 2004

(87) PCT Pub. No.: WO03/018014

PCT Pub. Date: Mar. 6, 2003

(65) Prior Publication Data

US 2004/0198636 A1     Oct. 7, 2004

Related U.S. Application Data (60) Provisional application No. 60/314,561, filed on Aug. 23, 2001.

(51) Int. Cl.
*A61K 31/44* (2006.01)
*A61K 38/00* (2006.01)

(52) U.S. Cl. .......................... 514/345; 514/2

(58) Field of Classification Search ................. 514/350
See application file for complete search history.

(56) References Cited

U.S. PATENT DOCUMENTS

| | | |
|---|---|---|
| 4,450,150 A | 5/1984 | Sidman |
| 5,021,404 A | 6/1991 | Folkman et al. |
| 5,206,343 A | 4/1993 | Henke et al. |
| 5,512,591 A * | 4/1996 | Halperin et al. ............ 514/399 |
| 5,610,146 A | 3/1997 | Henke et al. |

(Continued)

FOREIGN PATENT DOCUMENTS

FR     2775900 A1     9/1999

(Continued)

OTHER PUBLICATIONS

A Saaristo, et al. Oncogene (2000) 19, 6122-6129.*

(Continued)

*Primary Examiner*—Cecilía J. Tsang
*Assistant Examiner*—Andrew D. Kosar
(74) *Attorney, Agent, or Firm*—Leydig, Voit & Mayer, Ltd (57) ABSTRACT

A method of inhibiting formation of vascular channels in tissues and a method of inhibiting proliferation of a cell of a non-vascularized intraepithelial neoplasia, both of which methods comprise administering to the tissues or the cell a compound.

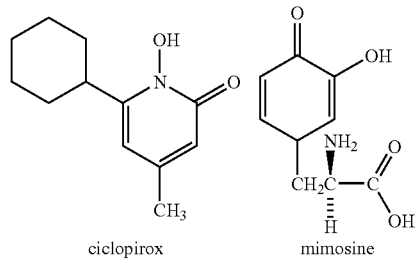

ciclopirox                mimosine

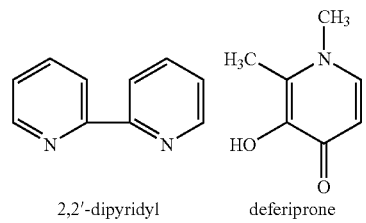

2,2'-dipyridyl            deferiprone

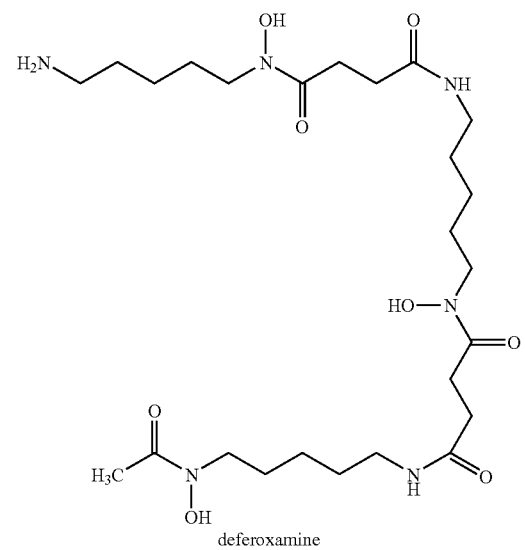

deferoxamine

67 Claims, 1 Drawing Sheet

U.S. PATENT DOCUMENTS

| | | | |
|---|---|---|---|
| 5,665,392 A * | 9/1997 | Kumar et al. | 424/489 |
| 5,789,426 A | 8/1998 | Hanauske-Abel et al. | |
| 6,004,986 A * | 12/1999 | Arthur et al. | 514/348 |
| 6,017,522 A * | 1/2000 | Butterfield et al. | 424/78.37 |
| 6,046,219 A | 4/2000 | Hanauske-Abel et al. | |
| 6,080,766 A | 6/2000 | Hanauske-Abel et al. | |
| 6,403,618 B1 | 6/2002 | Fernandez-Pol | |

FOREIGN PATENT DOCUMENTS

| | | | |
|---|---|---|---|
| WO | WO 8702580 A1 * | 5/1987 | |
| WO | WO 92/05190 A1 | 4/1992 | |
| WO | WO 99/03823 A2 | 1/1999 | |
| WO | WO 99/30562 A1 | 6/1999 | |
| WO | WO 02/064620 A2 | 8/2002 | |
| WO | WO 02/098853 A2 | 12/2002 | |
| WO | WO 2004007676 A2 * | 1/2004 | |

OTHER PUBLICATIONS

PMJ Clement, et al. Int. J. Cancer. (2002) 100, 491-498.*
T Linden and RH Wenger. Int. J. Cancer (2003) 106, 458-459.*
W. Zundel, et al. Genes & Development. (2001) 14( 4), pp. 391-396.*
Abbruzzese et al., "Deoxyhypusine Hydroxylase from Rat Testis," *J. Biol. Chem.*, 261(7), 3085-3089 (1986).
Andrus et al., "Antiretroviral Effects of Deoxyhypusyl Hydroxylase Inhibitors," *Biochem. Pharmacol.*, 55(11), 1807-1818 (1998).
Chen et al., "Biochemistry and Function of Hypusine Formation on Eukaryotic Initiation Factor 5A," *Biol. Signals*, 6, 105-109 (1997).
Chen et al., "$NAD^+$ Stimulated the Spermidine-Dependent Hypusine Formation on the 18 kDa Protein in Cytosolic Lysates Derived from NB-15 Mouse Neuroblastoma Cells," *FEBS Letters*, 229(2), 325-328 (1988).
Chvapil et al., "Effect of 1,10-Phenanthroline and Desferrioxamine In Vivo on Prolyl Hydroxylase and Hydroxylation of Collagen in Various Tissues of Rats," *Biochem. Pharmacol.*, 23, 2165-2173 (1974).
Csonga et al., "Evaluation of the Metal Ion Requirement of the Human Deoxyhypusine Hydroxylase from HeLa Cells using a Novel Enzyme Assay," *FEBS Lett.*, 380, 209-214 (1996).
Hanauske-Abel et al., "Inhibition of the G1-S Transition of the Cell Cycle by Inhibitors of Deoxyhypusine Hydroxylation," *Biochim. Biophys. Acta*, 1221, 115-124, (1994).
Hoffman et al., "A New Class of Reversible Cell Cycle Inhibitors," *Cytometry*, 12, 26-32 (1991).
Ingber et al., "Inhibition of Angiogenesis Through Modulation of Collagen Metabolism," *Lab. Invest.*, 59(1), 44-51 (1988).
Jastreboff et al., "Role of the Human Papilloma Virus in the Development of Cervical Intraepithelial Neoplasia and Malignancy," *Postgrad. Med. J.*, 78, 225-228 (2002).
Joura, "Epidemiology, Diagnosis and Treatment of Vulvar Intraepithelial Neoplasia," *Curr. Opin. Obstet. Gynecol.*, 14, 39-43 (2002).
Kivirikko et al., "Collagen Hydroxylases and the Protein Disulfide Isomerase Subunit of Prolyl 4-Hydroxylases," *Adv. Enzymol. Relat. Areas Mol. Biol.*, 72, 325-398 (1998).
Küffer et al., "Premalignant Lesions of the Oral Mucosa. A Discussion about the Place of Oral Intraepithelial Neoplasia (OIN)," *Oral Oncology*, 38, 125-130 (2002).
Lalande et al., "A New Compound which Reversibly Arrests T Lymphocyte Cell Cycle Near the $G_1$/S Boundary," *Exp. Cell. Res.*, 188, 117-121 (1990).
McCaffrey et al., "Specific Inhibition of eIF-5A and Collagen Hydroxylation by a Single Agent," *J. Clin. Invest.*, 95, 446-455 (1995).
Murphey et al., "Hypusine Formation in Protein by a Two-step Process in Cell Lysates," *J. Biol. Chem.*, 262, 15033-15036 (1987).
Park et al., "Hypusine Is Essential for Eukaryotic Cell Proliferation," *Biol. Signals*, 6, 115-123 (1997).
Park et al., "The Biosynthesis of Protein-bound Hypusine ($N^e$-(4-Amino-2-hydroxybutyl)Lysine)," *J. Biol. Chem.*, 257(12), 7217-7222 (1982).
Park et al., "Is Hypusine Essential for Eukaryotic Cell Proliferation?," *Trends Biochem. Sci.*, 18, 475-479 (1993).
Rosenbloom et al., "Inhibition of Proline Hydroxylation does not Inhibit Secretion of Tropoelastine by Chick Aorta Cells," *FEBS Lett.*, 65(2), 246-250 (1976).
Samuni et al., "Radiation Sensitization of Mammalian Cells by Metal Chelators," *Radiat. Res.*, 155, 304-310 (2001).
Solomon et al., "The 2001 Bethesda System: Terminology for Reporting Results of Cervical Cytology," *JAMA*, 287(16), 2114-2119 (2002).
Szeimies et al., "Behandlung von therapie-resistenten Verrucae vulgares mit eimen Ciclopirox-haltigen Lack," *Hautarzt*, 52, 489-491 (2001).
Wolff et al., "Deoxyhypusine Synthase from Rat Testis: Purification and Characterization," *J. Biol. Chem.*, 270(15), 8660-8666 (1995).
Ceschin-Roques et al., "Ciclopiroxolamine cream 1%: in vitro and in vivo penetration into the stratum corneum," *Skin Pharmacol.*, 4(2), 95-99 (1991).
Clement et al., The Antifungal Drug Ciclopirox Inhibits Deoxyhypusine and Proline Hydroxylation, Endothelial Cell Growth and Angiogenesis In Vivo, *Int. J. Cancer*, 100, 491-498 (2002).
Cracchiolo et al., "Eukaryotic initiation factor 5A-1 (eIF5A-1) as a diagnostic marker for aberrant proliferation in intraepithelial neoplasia of the vulva," *Gynecol. Oncol.*, 94(1), 217-222 (2004).
Fan et al., "Inhibition of N-*myc* Expression and Induction of Apoptosis by Iron Chelation in Human Neuroblastoma Cells," *Cancer Research*, 61(3), 1073-1079 (2001).
Gehse et al., "The effective epidermal inhibition depth of ciclopiroxolamine and naftifin in relation to a galenic preparation," *Mykosen*, 30(7), 322-325 (1987).
Georgalas, "Enhanced delivery of an anti-dandruff active in a shampoo vehicle," *J. Cosmet. Sci.*, 55 Suppl., S207-S214 (2004).
Harada et al., "Angiogenesis and vasodilation in skin warts. Association with HPV infection," *Anticancer Res.*, 20(6B), 4519-4523 (2000).
Harada et al., "VEGF expression in skin warts. Relevance to angiogenesis and vasodilation," *Arch. Dermatol. Res.*, 293(5), 233-238 (2001).
Hillebrand et al., "Inhibition of acute ornithine decarboxylase induction can predict tumor prevention by topical photoreceptive agents in the skin of hairless mice exposed to ultraviolet radiation," *J. Soc. Cosmet. Chem.*, 44(3), 129-138 (1993).
Kicic et al., "Effect of Iron Chelators on Proliferation and Iron Uptake in Hepatoma Cells," *Cancer*, 92(12), 3093-3110 (2001).
Le et al., "Competing pathways of iron chelation: angiogenesis or anti-tumor activity: targeting different molecules to induce specific effects," *Int J Cancer*, 110(3), 468-469 (2004).
Linden et al., The FASEB Journal express article 10. 1096/fj. 0586fje. Published online Feb. 19, 2003.
Linden et al., "The antimycotic ciclopirox olamine induces HIF-1alpha stability, VEGF expression, and angiogenesis," *FASEB J.*, 17(6), 761-763 (2003).
Macpherson et al., "Anti-angiogenic activity of human endostatin is HIF-1-independent in vitro and sensitive to timing of treatment in a human saphenous vein assay," *Mol. Cancer Ther.*, 2(9), 845-854 (2003).
Selections from the Physicians Desk Reference, 59th Ed., (2005).
Szeimies et al., "Treatment of recalcitrant common warts with a ciclopirox-containing lacquer,"*Hautarzt.*, 52(6), 489-491 (2001).
Cracchiolo et al., Clinical Protocol No. 0120050348, Grant No. 05-2405-CCR-EO, (1-20), University of New Jersey (2005).
Bevec et al., *Proc. Natl. Acad. Sci. USA*, 91, 10829-10833 (1994).
Bonte et al., *Arch Kriminol.*, 158, 163-174 (1976).
Caraglia et al., *Adv. Exp. Med. Biol.*, 472, 187-198 (1999).
Donfrancesco et al., *Anti-Cancer Drugs*, 4, 317-321 (1993).
Donfrancesco et al., *Anticancer Res.*, 15, 2347-2350 (1995).
Donfrancesco et al., *Cancer Res.*, 50, 4929-4930 (1990).
Folk et al., *J. Biol. Chem.*, 255 (8), 3695-3700 (1980).
Gho et al., *Cancer Res.*, 59, 5128-5132 (1999).

Grant et al., *J Cell. Physiol.*, 153, 614-625 (1992).
Guan et al., *Cancer Res.*, 61, 3806-3809 (2001).
Hanauske-Abel et al., *FEBS Lett.*, 366, 92-98 (1995).
Jakus et al., *J. Biol. Chem.*, 268 (18), 13151-13159 (1993).
Jue et al., *Drugs*, 29, 330-341 (1985).
Kalejta et al., *Exp Cell Res.*, 231, 173-183 (1997).
Kang et al., *J. Biol. Chem.*, 269, 3934-3940 (1994).
Kellner et al. *Arzneimittelforschung*, 31, 1337-1353 (1981).
Kivirikko et al., *Med Biol.*, 54, 159-186 (1976).
Kontoghiorghes et al., *Transfus Sci.*, 23, 211-223 (2000).
Kubota et al., *J. Cell Biol.*, 107, 1589-1598 (1988).
Lee et al., *J. Med. Chem.*, 38, 3053-3061 (1995).
Levenson et al., *Nucleic Acids Res.*, 21 (17), 3997-4004 (1993).
Lipowsky et al., *Embo J.*, 19, 4362-4371 (2000).
Liu et al., *Biol. Signals.*, 6, 166-174 (1997).
Park et al., *Biofactors*, 4, 95-104 (1993).
Park et al., *J. Biol. Chem.*, 269 (45), 27827-27832 (1994).
Rosorius et al., *J. Cell Sci.*, 112, 2369 2380 (1999).
Sakurai et al., *Chemotherapy*, 24, 68-76 (1978).
Samuni et al. *Radiat Res.*, 155, 304-310 (2001).
Skoog et al., *Eur. J. Biochem.*, 19, 81-89 (1971).
Tsvetkov et al., *Cancer Res.*, 57, 2252-2255 (1997).
Urbani et al., *Exp. Cell Res.*, 219, 159-168 (1995).
Wang et al., *Anticancer Res.*, 19, 445-450 (1999).
Xu et al., *J. Biol. Chem.*, 276 (4), 2555-2561 (2001).
Zuk et al., *Embo J.*, 17 (10)6, 2914-2925 (1998).

* cited by examiner

FIGURE 1 ciclopirox mimosine 2,2'-dipyridyl deferiprone deferoxamine

METHODS OF INHIBITING FORMATION OF VASCULAR CHANNELS AND METHODS OF INHIBITING PROLIFERATION

FIELD OF THE INVENTION

This invention pertains to methods of inhibiting formation of vascular channels in tissues and methods of inhibiting proliferation of a cell of a non-vascularized intraepithelial neoplasia.

BACKGROUND OF THE INVENTION

Deoxyhypusine hydroxylase is the enzyme that catalyzes the final step in the synthesis of hypusine, a unique post-translational modification essential for eukaryotic cell proliferation. Hypusine [$N^\epsilon$-(4-amino-2-hydroxybutyl)-lysine] occurs in a single cellular protein, eukaryotic translation initiation factor-5A(eIF-5A) (for reviews see Park et al., *Trends Biochem. Sci.* 18(12): 475–479 (1993); Park et al., *Biol. Signals* 6(3): 115–123 (1997); and Chen et al., *Biol. Signals* 6(3): 105–109 (1997)). It is formed in two enzymatic steps that occur immediately following translation of the eIF-5A precursor protein. In the first step, catalyzed by deoxyhypusine synthase, the intermediate deoxyhypusine is formed by nicotinamide adenine dinucleotide (NAD)-dependent transfer of the 4-aminobutyl moiety of the polyamine spermidine to the $\epsilon$-amino group of a specific lysine residue in the eIF-5A precursor (Chen et al., *FEBS Letters* 229(2): 325–328 (1988); Murphey et al., *J. Biol. Chem.* 262(31): 15033–15036 (1987); and Wolff et al., *J. Biol. Chem.* 270(15): 8660–8666 (1995)). The second step involves hydroxylation of the side chain of this intermediate by deoxyhypusine hydroxylase (Park et al., *J. Biol. Chem.* 257(12): 7217–7222 (1982); and Abbruzzese et al., *J. Biol. Chem.* 261(7): 3085–3089 (1986)).

Prolyl 4-hydroxylase (procollagen-proline dioxygenase) is a non-heme iron enzyme that catalyzes hydroxylation of proline residues in protocollagen to trans-4-hydroxy-L-proline, and thereby promotes triple helix formation, collagen secretion and deposition into the extracellular matrix (for a review see Kivirikko et al., *Adv. Enzymol. Relat. Areas Mol. Biol.* 72: 325–398 (1998)). It has been reported to be inhibited by several metal chelators, including mimosine, deferiprone, 2,2'-dipyridyl and deferoxamine, in vitro, or in cultured cells (McCaffrey et al., *J. Clin Invest.* 95(2): 446–55 (1995); U.S. Pat. No. 6,046,219; Chvapil et al., *Biochem. Pharmacol.* 23(15): 2165–73 (1974); and Rosenbloom et al., *FEBS Lett.* 65(2): 246–50 (1976)).

While it is known in the art that mimosine, ciclopirox and deferiprone, all of which are inhibitors of deoxyhypusine hydroxylase, have been shown to inhibit cell cycle progression in late G1 in certain mammalian cells (Hanauske-Abel et al., *Biochim. Biophys. Acta* 1221(2): 115–24 (1994); Andrus et al., *Biochem. Pharmacol.* 55(11): 1807–18 (1998); Lalande et al., *Exp. Cell. Res.* 188(1): 117–21 (1990); and Hoffman et al., *Cytometry* 12(1): 26–32 (1991)), until now it has not been known whether inhibitors of deoxyhypusine hydroxylase can inhibit proliferation of cells of a non-vascularized intraepithelial neoplasia. Furthermore, while it is known in the art that mimosine can additionally inhibit prolyl 4-hydroxylase and collagen biosynthesis in human smooth muscle, causing arrest of capillary formation, until now it has not been known whether ciclopirox and derivatives thereof, as well as other inhibitors of prolyl 4-hydroxylase, can inhibit the formation of vascular channels in tissues.

It has now been discovered that proliferation of cells of a non-vascularized intraepithelial neoplasia can be inhibited. It also has been discovered that the formation of vascular channels in tissues can be inhibited. In view of these discoveries, the present invention seeks to provide a method of inhibiting proliferation of a cell of a non-vascularized intraepithelial neoplasia and a method of inhibiting the formation of vascular channels. These and other objects and advantages of the invention, as well as additional inventive features, will be apparent from the description of the invention provided herein.

BRIEF SUMMARY OF THE INVENTION

The present invention provides a method of inhibiting formation of vascular channels in tissues. The method comprises administering to the tissues a compound, which inhibits both deoxyhypusine hydroxylase and prolyl 4-hydroxylase, in an amount effective for inhibiting formation of vascular channels. Through this method, the formation of vascular channels in the tissues is inhibited.

Further provided by the present invention is a method of inhibiting proliferation of a cell of a non-vascularized intraepithelial neoplasia. The method comprises administering to the cell a compound, which inhibits both deoxyhypusine hydroxylase and prolyl 4-hydroxylase, in an amount effective for inhibiting proliferation. Through this method, proliferation of the cell is inhibited.

Still further provided is another method of inhibiting formation of vascular channels in tissues. This method comprises administering to the tissues a compound of Formula I, Formula I wherein $R_1$, $R_2$, $R_3$, and $R_4$ can be the same or different and each is (i) a hydrogen, (ii) an alkyl, alkenyl, or alkoxy group, any of which contains 1 to about 8 carbon atoms, (iii) an aryl, carbamyl, aminocarbonyl, aralkyl, or cycloalkyl group, any of which contains 5 to about 12 carbon atoms, (iv) an alkoxycarbonyl, carbamyl, aminocarbonyl, alkylaminocarbonyl, or arylaminocarbonyl group, any of which contains up to about 15 carbon atoms, (v) a peptide or peptidomimetic moiety, either of which contains 10 to about 100 carbon atoms, or (vi) a salt, ester, or amide of any of the compounds of (i)–(v). The compound of Formula I is administered in an amount effective for inhibiting the formation of vascular channels. Upon this method, the formation of vascular channels in the tissues is inhibited.

Yet still further provided is another method of inhibiting formation of vascular channels in tissues. This method comprises administering to the tissues a compound of Formula II, Formula II wherein $R_5$ is a hydrogen, or an aminocarbonyl, alkylaminocarbonyl, or arylaminocarbonyl moiety, any of which contains up to about 15 carbon atoms; $R_6$, $R_7$ and $R_8$ can be the same or different and each is a hydrogen or an acetyl moiety. The compound of Formula II is administered in an amount effective for inhibiting the formation of vascular channels. Upon this method, the formation of vascular channels in the tissues is inhibited.

The present invention further provides yet another method of inhibiting formation of vascular channels in tissues. This method comprises administering to the tissues a compound of Formula III, Formula III wherein $R_9$, $R_{10}$, $R_{11}$, and $R_{12}$ can be the same or different and each is a hydrogen, a hydroxyl, or an alkoxycarbonyl, aminocarbonyl, alkylaminocarbonyl, or arylaminocarbonyl moiety, any of which contains up to about 15 carbons. The compound of Formula III is administered in an amount effective for inhibiting the formation of vascular channels. Upon this method, the formation of vascular channels in the tissues is inhibited.

The present invention provides yet another method of inhibiting proliferation of a cell of a non-vascularized intraepithelial neoplasia. The method comprises administering to the cell a compound of Formula I, Formula I wherein $R_1$, $R_2$, $R_3$, and $R_4$ can be the same or different and each is (i) a hydrogen, (ii) an alkyl, alkenyl, or alkoxy group, any of which contains 1 to about 8 carbon atoms, (iii) an aryl, carbamyl, aminocarbonyl, aralkyl, or cycloalkyl group, any of which contains 5 to about 12 carbon atoms, (iv) an alkoxycarbonyl, carbamyl, aminocarbonyl, alkylaminocarbonyl, or arylaminocarbonyl group, any of which contains up to about 15 carbon atoms, (v) a peptide or peptidomimetic moiety, either of which contains 10 to about 100 carbon atoms, or (vi) a salt, ester, or amide of any of the compounds of (i)–(v). The compound of Formula I is administered in an amount effective for inhibiting proliferation. Upon this method, proliferation of the cell is inhibited.

Still further provided is another method of inhibiting proliferation of a cell of a non-vascularized intraepithelial neoplasia. This method comprises administering to the cell a compound of Formula II, Formula II wherein $R_5$ is a hydrogen, or an aminocarbonyl, alkylaminocarbonyl, or arylaminocarbonyl moiety, any of which contains up to about 15 carbon atoms; $R_6$, $R_7$ and $R_8$ can be the same or different and each is a hydrogen or an acetyl moiety. The compound of Formula II is administered in an amount effective inhibiting proliferation. Upon this method, proliferation of the cell is inhibited.

The present invention further provides yet another method of inhibiting proliferation of a cell of a non-vascularized intraepithelial neoplasia. This method comprises administering to the cell a compound of Formula III, Formula III wherein $R_9$, $R_{10}$, $R_{11}$, and $R_{12}$ can be the same or different and each is a hydrogen, a hydroxyl, or an alkoxycarbonyl, aminocarbonyl, alkylaminocarbonyl, or arylaminocarbonyl moiety, any of which contains up to about 15 carbons. The compound of Formula III is administered in an amount effective for inhibiting proliferation. Upon this method, proliferation of the cell is inhibited.

Still further provided is yet another method of inhibiting proliferation of a cell of a non-vascularized intraepithelial neoplasia. This method comprises administering to the cell a compound of Formula IV, Formula IV wherein $R_{13}$, $R_{14}$, $R_{15}$, and $R_{16}$ can be the same or different and each is (i) a hydrogen, (ii) an alkyl, alkenyl, or alkoxy group, any of which contains 1 to about 8 carbon atoms, (iii) an aryl, carbamyl, aminocarbonyl, aralkyl, or cycloalkyl group, any of which contains 5 to about 12 carbon atoms, (iv) an alkoxycarbonyl, carbamyl, aminocarbonyl, alkylaminocarbonyl, or arylaminocarbonyl group, any of which contains up to about 15 carbon atoms, (v) a peptide or peptidomimetic moiety, either of which contains 10 to about 100 carbon atoms, or (vi) a salt, ester, or amide of any of the compounds of (i)–(v). The compound of Formula IV is administered in an amount effective for inhibiting proliferation. Upon this method, proliferation of the cell is inhibited.

DETAILED DESCRIPTION OF THE INVENTION

Figure 1:
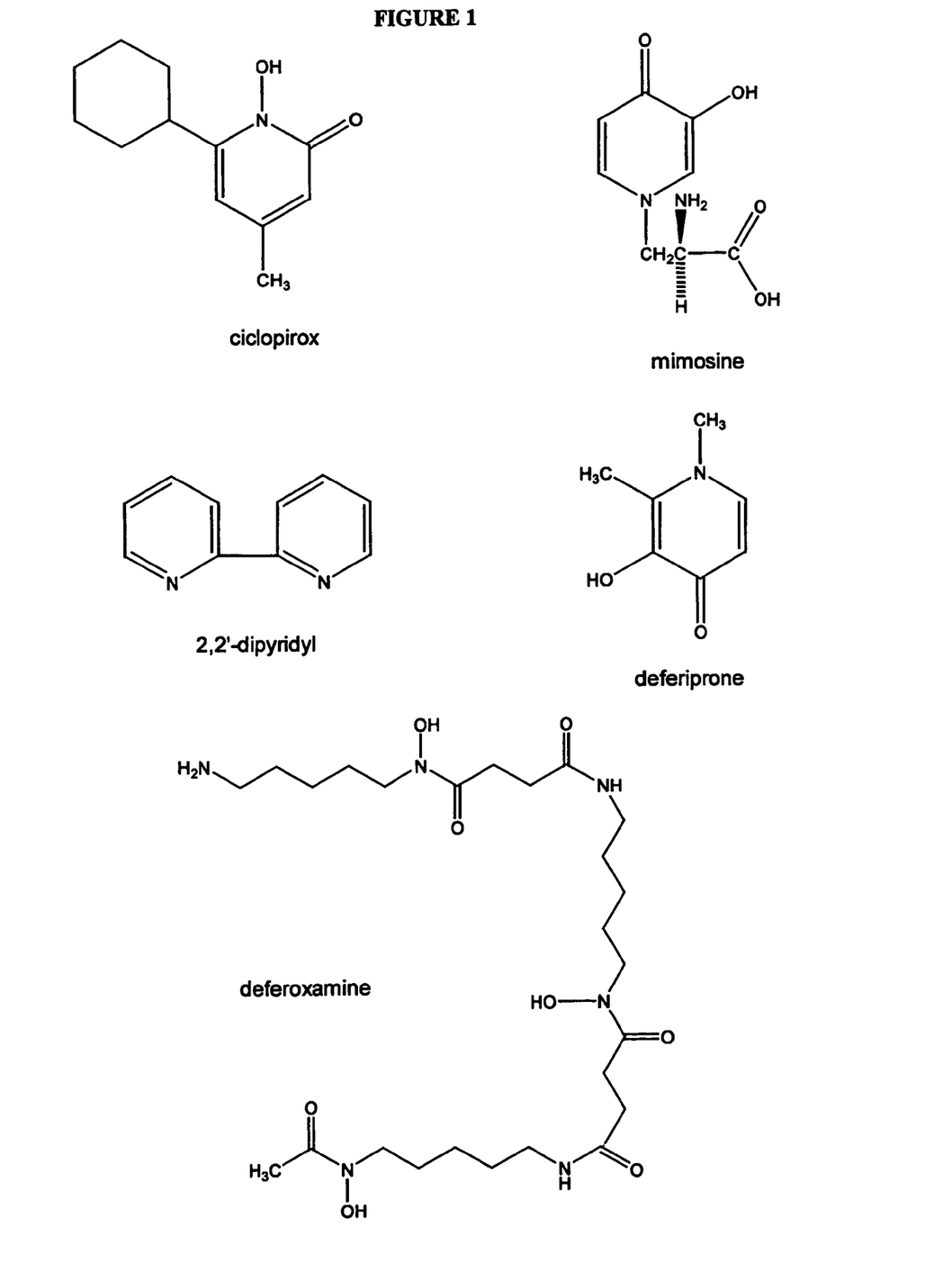
FIG. 1 represents chemical structures of ciclopirox, mimosine, 2,2'-dipyridyl, deferiprone, and deferoxamine.

The present invention provides a method of inhibiting formation of vascular channels in tissues. The method comprises administering to the tissues a compound, which inhibits both deoxyhypusine hydroxylase and prolyl 4-hydroxylase, in an amount effective for inhibiting the formation of vascular channels. Upon this method, the formation of a vascular channels in the tissues is inhibited.

The term "vascular channel" as used herein, refers to any canalicular structure, displaying a lining of specialized cells for the purpose of directional flow of blood or blood components that is required for the formation and maintenance of any form of a tissue. Such channels are required for the growth of any mass of tissue exceeding a few mm in diameter. Vascular channels include, but are not limited to, lymphatic channels, arteriolar channels, venolar channels, and capillaries. The term "tissue" as used herein includes both embryonic and adult tissue.

In a preferred embodiment of the present inventive method, the compound is a compound of Formula I, Formula I wherein $R_1$, $R_2$, $R_3$, and $R_4$ can be the same or different and each is (i) a hydrogen, (ii) an alkyl, alkenyl, or alkoxy group, any of which contains 1 to about 8 carbon atoms, (iii) an aryl, carbamyl, aminocarbonyl, aralkyl, or cycloalkyl group, any of which contains 5 to about 12 carbon atoms, (iv) an alkoxycarbonyl, carbamyl, aminocarbonyl, alkylaminocarbonyl, or arylaminocarbonyl group, any of which contains up to about 15 carbon atoms, (v) a peptide or peptidomimetic moiety, either of which contains 10 to about 100 carbon atoms, or (vi) a salt, ester, or amide of any of the compounds of (i)–(v). Preferably, the compound of Formula I is ciclopirox, which is also known in the art as ciclopirox olamine.

In another embodiment of the present inventive method, the compound is a compound of Formula II, Formula II wherein $R_5$ is a hydrogen, or an aminocarbonyl, alkylaminocarbonyl, or arylaminocarbonyl moiety, any of which contains up to about 15 carbon atoms; $R_6$, $R_7$ and $R_8$ can be the same or different and each is a hydrogen or an acetyl moiety. Preferably, the compound of Formula II is deferoxamine, which is also known in the art as desferrioxamine or deferoxamine mesylate.

In yet another embodiment, the compound is a compound of Formula III,

Formula III wherein $R_9$, $R_{10}$, $R_{11}$, and $R_{12}$ can be the same or different and each is a hydrogen, a hydroxyl, or an alkoxycarbonyl, aminocarbonyl, alkylaminocarbonyl, or arylaminocarbonyl moiety, any of which contains up to about 15 carbons. Preferably, the compound of Formula III is 2,2'-dipyridyl, which is also known in the art as $\alpha,\alpha'$ dipyridyl.

With respect to the present inventive methods, the tissue can be a tissue of any living system. However, it is preferred that the tissue is a tissue of a mammal. For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Furthermore, the tissue can be a tissue of any type, such that the tissue comprises cells of any type. However, it is preferred that the tissue is a tissue of an epithelial origin. Particularly, it is preferred that the tissue is a surface epithelium. Moreover, the tissue of the present inventive methods can be in vivo or ex vivo. The term "in vivo" as used herein means that the tissue is found within a living system. The term "ex vivo" as used herein means that the tissue is derived from a living system but is taken out of the living system.

The present invention further provides a method of inhibiting proliferation of a cell of a non-vascularized intraepithelial neoplasia. The method comprises administering to the cell a compound, which inhibits both deoxyhypusine hydroxylase and prolyl 4-hydroxylase, in an amount effective for inhibiting proliferation. Upon this method, proliferation of the cell is inhibited.

The term "non-vascularized" as used herein refers to an absence of vascular channels. The term "intraepithelial neoplasia" as used herein means the abnormal growth of the epithelial tissue on the surface of an organ. Intraepithelial neoplasias include, but are not limited to, cervical intraepithelial neoplasia, oral intraepithelial neoplasia, vulvar intraepithelial neoplasia, and rectal intraepithelial neoplasia (see, for instance, Solomon et al., *JAMA* 287(16): 2114–2119 (2002); Joura, *Curr. Opin. Obstet. Gynecol.* 14: 39–43 (2002); Kuffer et al., *Oral Oncology* 38: 125–130 (2002); and Jastreboff et al., *Postgrad. Med. J.* 78: 225–228 (2002)).

In a preferred embodiment of the present inventive method of inhibiting proliferation, the compound is a compound of Formula I, Formula I wherein $R_1$, $R_2$, $R_3$, and $R_4$ can be the same or different and each is (i) a hydrogen, (ii) an alkyl, alkenyl, or alkoxy group, any of which contains 1 to about 8 carbon atoms, (iii) an aryl, carbamyl, aminocarbonyl, aralkyl, or cycloalkyl group, any of which contains 5 to about 12 carbon atoms, (iv) an alkoxycarbonyl, carbamyl, aminocarbonyl, alkylaminocarbonyl, or arylaminocarbonyl group, any of which contains up to about 15 carbon atoms, (v) a peptide or peptidomimetic moiety, either of which contains 10 to about 100 carbon atoms, or (vi) a salt, ester, or amide of any of the compounds of (i)–(v). Preferably, the compound of Formula I is ciclopirox.

In an alternative embodiment of the present inventive method of inhibiting proliferation of a cell of a non-vascularized intraepithelial neoplasia, the compound is a compound of Formula II, Formula II wherein $R_5$ is a hydrogen, or an aminocarbonyl, alkylaminocarbonyl, or arylaminocarbonyl moiety, any of which contains up to about 15 carbon atoms; $R_6$, $R_7$ and $R_8$ can be the same or different and each is a hydrogen or an acetyl moiety. Preferably, the compound of Formula II is deferoxamine.

In yet another preferred embodiment of the present inventive method of inhibiting proliferation, the compound is a compound of Formula III, Formula III wherein $R_9$, $R_{10}$, $R_{11}$, and $R_{12}$ can be the same or different and each is a hydrogen, a hydroxyl, or an alkoxycarbonyl, aminocarbonyl, alkylaminocarbonyl, or arylaminocarbonyl moiety, any of which contains up to about 15 carbons. Preferably, the compound of Formula III is 2,2'-dipyridyl.

In still yet another preferred embodiment of the present inventive method of inhibiting proliferation, the compound is a compound of Formula IV, Formula IV wherein $R_{13}$, $R_{14}$, $R_{15}$, and $R_{16}$ can be the same or different and each is (i) a hydrogen, (ii) an alkyl, alkenyl, or alkoxy group, any of which contains 1 to about 8 carbon atoms, (iii) an aryl, carbamyl, aminocarbonyl, aralkyl, or cycloalkyl group, any of which contains 5 to about 12 carbon atoms, (iv) an alkoxycarbonyl, carbamyl, aminocarbonyl, alkylaminocarbonyl, or arylaminocarbonyl group, any of which contains up to about 15 carbon atoms, (v) a peptide or peptidomimetic moiety, either of which contains 10 to about 100 carbon atoms, or (vi) a salt, ester, or amide of any of the compounds of (i)–(v). Preferably, the compound of Formula IV is deferiprone, which is also known in the art as 1,2-dimethyl-3-hydroxypyrid-4-one, L1, or CP20.

For purposes of the present inventive method of inhibiting proliferation, the non-vascularized intraepithelial neoplasia can be found in any part of any living system. However, it is preferred that the intraepithelial neoplasia is derived from a mammal as described herein. Preferably, the mammal is a human. It is furthermore preferred that the non-vascularized intraepithelial neoplasia is found in an oronasopharynx, a gastrointestinal tract, or an urogenital tract. The oronasopharynx includes the anatomical system that extends from the oral cavity and all its contents to the nasal passages, and the area where oral cavity and nasal passages combine, plus all associated glands and organs. The gastrointestinal tract includes the anatomical system that extends from the oronasopharynx to the anus, plus all associated glands and organs. The urogenital tract includes the anatomical system that extends from the kidneys and the gonads (ovaries, testes) to the body surface, plus all associated glands and organs. In the instance that the non-vascularized intraepithelial neoplasia is found in the urogenital tract, it is preferred that the neoplasia is found in either a cervix, vagina, or a vulva. Furthermore, the cell can be either in vivo or ex vivo.

For purposes of all of the present inventive methods, the amount or dose of the compound administered should be sufficient to effect a therapeutic response in the animal over a reasonable time frame. Particularly, the dose of the compound of any of Formula I, Formula II, Formula III, and Formula IV should be sufficient to inhibit formation of vascular channels in tissues or to inhibit proliferation of a cell of a non-vascularized intraepithelial neoplasia within about 24 to about 48 hours, if not 3–6 days, from the time of administration. The dose will be determined by the efficacy of the particular compound and the condition of the animal (e.g., human), as well as the body weight of the animal (e.g., human) to be treated. Many assays for determining an administered dose are known in the art. For purposes of the present invention, an assay, which comprises comparing the extent to which cell proliferation is inhibited in a tissue upon administration of a given dose of a compound to a mammal among a set of mammals that are each given a different dose of the compound, could be used to determine a starting dose to be administered to a mammal. The extent to which cell proliferation is inhibited upon administration of a certain dose can be assayed as described herein as Example 4.

The size of the dose also will be determined by the existence, nature and extent of any adverse side effects that might accompany the administration of a particular compound. Ultimately, the attending physician will decide the dosage of the compound of the present invention with which to treat each individual patient, taking into consideration a variety of factors, such as age, body weight, general health, diet, sex, inhibitor to be administered, route of administration, and the severity of the condition being treated.

One skilled in the art will appreciate that suitable methods of administering a compound of the present invention are known, and, although more than one route can be used to administer a particular composition, a particular route can provide a more immediate and more effective response than another route.

Formulations suitable for oral administration can consist of (a) liquid solutions, such as an effective amount of the compounds dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized)

condition requiring only the addition of the sterile liquid carrier, for example, water, for injections, immediately prior to use. Extemporaneous injection solutions and suspensions can be prepared from sterile powders, granules, and tablets of the kind previously described.

With respect to all of the present inventive methods, the 2,2'-dipyridyl and the ciclopirox are administered topically, whereas the deferoxamine is administered systemically, i.e., intravenously or subcutaneously. Deferiprone may be used systemically, and/or topically.

Furthermore, all of the present inventive methods can comprise the administration of the compound, in the presence or absence of an agent that enhances its efficacy, or the methods can further comprise the administration of other suitable components, such as radiation therapy or chemotherapy with another active agent. The term "radiation therapy" as used herein refers to the treatment of disease (especially cancer) by exposure to radiation. The term "chemotherapy" as used herein refers to the treatment of cancer using specific chemical agents or drugs that are destructive of malignant cells and tissues. Also, "chemotherapy" refers to the treatment of disease using chemical agents or drugs that are toxic to the causative agent of the disease, such as a virus, bacterium, or other microorganism.

If combined with radiation therapy or chemotherapy, the compounds of the present invention can be administered simultaneously or sequentially. The term "sequentially" as used herein refers to the compound being administered either before or after the radiation therapy or chemotherapy. Preferably, the compound is administered first, particularly if combined with radiation therapy.

The present inventive method of inhibiting formation of vascular channels can further comprise surgical removal of an abnormal growth in which it is desirable to inhibit the formation of vascular channels. In this case the compound is desirably administered prior to the surgical removal of the abnormal growth. The term "abnormal growth" as used herein, refers to any mass of tissue comprising cells that are growing or have grown in an unregulated manner. Abnormal growths include, but are not limited to, tumors, fibroids, polyps, cysts, warts, and the like.

Likewise, the present inventive method of inhibiting proliferation of a cell of a non-vascularized intraepithelial neoplasia can further comprise surgical removal of the intraepithelial neoplasia. In this case the compound is desirably administered prior to the surgical removal of the intraepithelial neoplasia.

The compounds of the present inventive methods are known in the art and are, in general, commercially available. For instance, ciclopirox, 2,2'-dipyridyl, and deferoxamine can be purchased from Sigma (St. Louis, Mo.). Deferiprone can be purchased from Apotex (Toronto, Ontario).

One of ordinary skill in the art will readily appreciate that each compound of the present inventive methods can be modified in any number of ways, such that the therapeutic efficacy of the compound is increased through the modification. For instance, the compound could be conjugated either directly or indirectly through a linker to a targeting moiety. The practice of conjugating compounds to targeting moieties is known in the art. See, for instance, Wadwa et al., J. Drug Targeting 3: 111 (1995), and U.S. Pat. No. 5,087, 616. The term "targeting moiety" as used herein, refers to any molecule or agent that specifically recognizes and binds to a cell-surface receptor, such that the targeting moiety directs the delivery of the compound to a population of cells on which surface the receptor is expressed. Targeting moieties include, but are not limited to, antibodies, or fragments thereof, peptides, hormones, growth factors, cytokines, and any other naturally- or non-naturally-existing ligands, which bind to cell surface receptors. The term "linker" as used herein, refers to any agent or molecule that bridges the compound to the targeting moiety. One of ordinary skill in the art recognizes that sites on the compounds, which are not necessary for the function of the compound, are ideal sites for attaching a linker and/or a targeting moiety, provided that the linker and/or targeting moiety, once attached to the compound, do(es) not interfere with the function of the compound, i.e., the ability to inhibit formation of vascular channels in tissues or the ability to inhibit proliferation of a cell of a non-vascularized intraepithelial neoplasia For purposes of the present invention, the ideal sites of attachment for compounds of Formula I are denoted below with an "W":

Ideal sites for attaching a linker and/or a targeting moiety onto compounds of Formula II are denoted below with an "X":

For compounds of Formula III, ideal sites of attachment are denoted below with a "Y".

Finally, ideal sites for compounds of Formula IV are denoted below with a "Z":

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous material, such as a polymer, wherein the compound is encapsulated by or diffused throughout the porous material. The depot is then implanted into the desired location within the body and the compound is released from the implant at a predetermined rate by diffusing through the porous material.

As used herein, the term "inhibit," and words stemming therefrom, do not necessarily imply 100% or complete inhibition. Rather, there are varying degrees of inhibition of which one of ordinary skill in the art recognizes as having a potential benefit or therapeutic effect. In this regard, the inhibition of the formation of vascular channels in tissues achieved by the present inventive method can be an inhibition of any level. Likewise, the inhibition of proliferation of a cell of a non-vascularized intraepithelial neoplasia can constitute any degree of inhibition. Preferably, the levels of inhibition are above 25%. More preferred, the inhibitions achieved by the subject methods are greater than 50%. Most preferred is that the inhibition of formation of vascular channels in tissues and the inhibition of proliferation achieved by these methods are more than 90%. Similarly, the inhibition of both deoxyhypusine hydroxylase and prolyl 4-hydroxylase can vary in extent and does not necessarily have to be complete inhibition. Preferably, the inhibition of these enzymes is greater than 25%. More preferably, the inhibition of these enzymes is greater than 50%. Most preferred is that the inhibition of the enzymes is greater than 90%.

EXAMPLES

The following examples further illustrate the invention but, of course, should not be construed as in any way limiting its scope.

Abbreviations

For convenience, the following abbreviations are used herein:

EIF-5A, eukaryotic translation initiation factor-5A; NAD, nicotinamide adenine dinucleotide; HUVEC, primary human vascular endothelial cells; EBM-2, endothelial cell basal medium; ATCC, American Type Culture Collection; VEGF, vascular endothelial growth factor; hFGF-β, human fibroblast growth factor-beta; hEGF, human epidermal growth factor; $IC_{50}$, inhibitory concentration 50; PBS, phosphate-buffered saline.

Example 1

This example describes the materials and formulae used in the following examples.

Cells and Reagents

HUVEC and endothelial cell media bullet kits including EBM-2 and supplements (SingleQuots) were purchased from Biowhittaker/Clonetics (Walkersville, Md.). Siha cells (ATCC #HTB-35), which are human squamous epithelial carcinoma cells from the cervix, were purchased from the American Type Culture Collection (ATCC) (Manassas, Va.). Ciclopirox olamine, L-mimosine, 2,2'-dipyridyl, deferoxamine mesylate, ascorbic acid, β-aminopropionitrile, trans-4-hydroxy-L-proline and L-proline were obtained from Sigma (St-Louis, Mo.). [1,8-$^3$H]spermidine (44.5 Ci/mmol) and [methyl-$^3$H]thymidine (85.4 Ci/mmol) were obtained from Dupont/New England Nuclear (Boston, Mass.), and L-[2,3,4,5-$^3$H]proline (105 Ci/mmol) from Amersham Pharmacia Biotech (Piscataway, N.J.). Deferiprone was kindly supplied by Dr. M. Spino (Apotex, Toronto, Canada). Matrigel was purchased from Becton & Dickinson Biosciences (Bedford, Mass.). Glass TLC plates (20×20 cm) coated with silica gel (LKGF, 250 micron) were from Whatman (Clifton, N.J.).

Cell Culture

HUVEC were maintained in supplemented EBM-2 (2% fetal bovine serum, and SingleQuots containing hydrocortisone, insulin-like growth factor 1, heparin, VEGF, ascorbic acid, hFGF-β and hEGF) at 37° C., 5% $CO_2$. All experiments were conducted with cells between passages four and seven. Siha cells were cultured in accordance with the instructions given by the ATCC.

Calculation of Inhibitory Concentration 50 ($IC_{50}$)

For determination of the $IC_{50}$ value, the data of each separate experiment were fitted for each in compound in the equation y=(100ax)/(1+ax), using Kaleidagraph software.

Example 2

This example demonstrates the concentration-dependent inhibition of deoxyhypusine hydroxylase by ciclopirox, mimosine, deferiprone, deferoxamine, and 2,2'-dipyridyl.

Exponentially growing HUVEC (5×10$^5$ cells per 60-mm dish) were incubated with 5 μCi/ml of [1,8-$^3$H]spermidine for 18 h in the presence or absence of the indicated concentrations of inhibitors. The cells were washed with PBS and harvested by centrifugation at 300×g for 5 minutes. Cellular proteins were precipitated with 10% trichloroacetic acid containing 1 mM each of unlabeled spermidine, spermine and putrescine, and the precipitates were washed three times to remove radiolabeled free polyamines. The washed precipitates were hydrolyzed in 6 N HCl for 18 h at 115° C. Radiolabeled hypusine and deoxyhypusine released by acid hydrolysis were separated by ion exchange chromatography using an automated Dionex D-400 amino acid analyzer (Park et al., (1982), supra). The radioactivity in the hypusine and the deoxyhypusine fractions was measured using a Beckman liquid scintillation spectrometer.

When exponentially growing HUVEC were incubated with ciclopirox and [$^3$H]spermidine for 20 h, concentration-dependent inhibition of deoxyhypusine hydroxylation was observed. In control HUVEC and in HUVEC treated with 2.5 μM or less of ciclopirox, only [$^3$H]hypusine but no [$^3$H]deoxyhypusine was detected in the cellular protein hydrolysates. At higher concentrations (5–100 μM), accumulation of the intermediate, [$^3$H]deoxyhypusine, with concomitant reduction of [$^3$H]hypusine, resulted from the inhibition of deoxyhypusine hydroxylase by ciclopirox. The IC$_{50}$ for this inhibition was ~5 μM and no [$^3$H]hypusine was detectable at >10 μM, suggesting a complete inhibition of deoxyhypusine hydroxylase. The total amount of radioactivity incorporated into the substrate protein (the sum of [$^3$H]hypusine and [$^3$H]deoxyhypusine) was comparable to the control value up to 5 μM of ciclopirox, but was noticeably lower at higher concentrations, presumably due to reduced eIF-5A precursor protein synthesis.

Mimosine, deferoxamine, deferiprone and 2,2'-dipyridyl also inhibited deoxyhypusine hydroxylation in HUVEC. However, these compounds were much less effective than ciclopirox. Although each compound exerted inhibition in a concentration-dependent manner, the efficacy varied widely with IC$_{50}$ values of 5, 16, 26, 117 and 191 μM for ciclopirox, deferoxamine, 2,2'-dipyridyl, deferiprone and mimosine, respectively.

Example 3

This example demonstrates the dose-dependent inhibition of proline hydryoxylation by ciclopirox, mimosine, deferiprone, deferoxamine, and 2,2'-dipyridyl.

For the determination of collagen proline 4-hydroxylation, exponentially growing HUVEC were plated in 60-mm dishes. After cell attachment, ascorbic acid (50 μg/ml), β-aminopropionitrile (30 μg/ml), and the test compounds were added along with [$^3$H]proline (20 μCi/ml). After an 18-h incubation, labeled proteins (including collagen) released into the medium were precipitated with 10% trichloroacetic acid. After washing three times with 5% trichloroacetic acid solution, the precipitated proteins were hydrolyzed in 6N HCl at 115° C. for 24 h. Unlabeled hydroxyproline was added to each sample. Radioactive proline and hydroxyproline were separated by thin layer chromatography on silica gel-coated glass plates in 75% phenol (phenol:water, 75:25 w/w) containing 0.2 mg/ml NaCN (Brenner et al., *Dünnschict-Chromatographie von Aminosäuren. Experientia* 16: 378–383 (1960). The positions of proline and hydroxyproline were visualized by the ninhydrin reaction. Hydroxyproline separated from proline with Rf values of 0.45 and 0.58, respectively. The silica gel in the hydroxyproline and proline areas was scraped off, eluted with 0.5 ml of water, and the radioactivity in each spot was counted. The degree of proline hydroxylation was estimated from the ratio of [$^3$H]hydroxyproline to the total radioactivity in [$^3$H]proline plus [$^3$H]hydroxyproline.

The formation of 4-hydroxyproline in collagen by HUVEC and the inhibition by ciclopirox and other test compounds were evident by the results of this experiment. [$^3$H]Hydroxyproline was detected in the proteins secreted from HUVEC after culture with [$^3$H]proline for 18–20 h. Even with the addition of ascorbic acid to stimulate collagen synthesis, and of the lysine oxidase inhibitor β-aminopropionitrile to prevent deposition of collagen into the extracellular matrix, the amount of [$^3$H]hydroxyproline was low (~2% of the total radioactivity in [$^3$H]proline and [$^3$H] hydroxyproline) in the proteins secreted into the medium, thus indicating a low rate of collagen synthesis by these cells. Inhibition of proline hydroxylation seemed to be less sensitive than that of deoxyhypusine hydroxylation. The relative inhibition of the two enzymes did not follow an exactly parallel pattern. Nevertheless, concentration-dependent inhibition of [$^3$H]hydroxyproline formation could be detected with each compound. The inhibition was in the order: ciclopirox>2,2'-dipyridyl>deferiprone=deferoxamine>mimosine. Ciclopirox again was the most effective of these compounds in the inhibition of proline hydroxylation, with 63% inhibition at 10 μM. Mimosine, the weakest inhibitor, showed only minor inhibition even at 400 μM. Interestingly, deferoxamine, a strong inhibitor of deoxyhypusine hydroxylase (IC$_{50}$, ~16 μM), was rather weak in the inhibition of proline hydroxylation (only 40% inhibition at 100 μM). This may reflect the different accessibility of the two protein hydroxylases or of the metals in their active sites to deferoxamine.

Example 4

This example demonstrates the concentration-dependent inhibition of DNA synthesis by ciclopirox, mimosine, deferiprone, deferoxamine, and 2,2'-dipyridyl.

The test compounds were added at the indicated concentrations to exponentially growing HUVEC in 24-well plates (1×10$^5$ cells/well). At 10 h, [$^3$H]thymidine (1 μCi/well) was added. After an additional 2-h incubation, the cells were washed twice with PBS. DNA was precipitated with 5% trichloroacetic acid, washed once with 5% trichloroacetic acid, and dissolved in 0.2 ml of 0.2 N NaOH for measurement of radioactivity.

The effects of ciclopirox and the other test compounds on DNA synthesis in HUVEC were compared. At 18 h of treatment all compounds caused inhibition of DNA synthesis in a concentration-dependent manner. Ciclopirox showed the strongest inhibition of DNA synthesis with an IC$_{50}$ of ~10 μM. The order of inhibition was ciclopirox>deferoxamine>2,2'-dipyridyl>deferiprone>mimosine with IC$_{50}$ values, 10, 16, 55, 130 and 455 μM, respectively. This order corresponds to the order of inhibition of deoxyhypusine hydroxylation, but not to that of proline hydroxylation.

Example 5

This example demonstrates the arrest in cell cycle progression by ciclopirox, mimosine, deferiprone, deferoxamine, and 2,2'-dipyridyl.

Exponentially growing HUVEC were treated with the test compounds for 24 or 48 h, and processed for cell cycle analysis. After harvesting cells by trypsin treatment, isolation and staining of cell nuclei were performed using a CycleTEST™ PLUS DNA Reagent Kit (Becton & Dickinson, Rutherford, N.J.), according to the procedure recommended by the manufacturer. Briefly, nuclei were released from cells by treatment with a nonionic detergent and trypsin. The nuclear chromatin was stabilized with spermine. Propidium iodide was used to stain the DNA. Fluorescence histograms were generated with a FACSCalibur cytometer (Becton & Dickinson, Rutherford, N.J.), using CELLQuest software.

These inhibitors caused changes in the cell cycle in HUVEC. The effects of inhibition of DNA synthesis are reflected in the change in the cell cycle distribution pattern, i.e., an increase of cell population in G1 with a reduction in both S and G2/M. After 24-h treatment with the compounds, G1/S arrest was evident with ciclopirox, deferoxamine, 2,2'-dipyridyl, and deferiprone, following the same order of effectiveness as the inhibition of DNA synthesis and of hypusine formation. Cell cycle effects were dependent on the inhibitor concentration and the incubation time. The concentrations that gave close to the maximum accumulation (>70%) of HUVEC in G1 at 24 h of treatment were 30, 50, 100, and 200 μM, for ciclopirox, deferoxamine, 2,2'-dipyridyl and deferiprone, respectively. At these concentrations, the inhibition of DNA synthesis was almost complete.

A G1/S arrest could be detected at lower concentrations for each compound if the incubation time was extended to 48 h. For example, a cell cycle arrest was achieved after treatment with 10 µM ciclopirox for 48 h, which was similar to that obtained at 24 h with 30 µM of the inhibitor. The cell cycle profile in mimosine-treated cells appeared to be somewhat different from those treated with other inhibitors. In contrast to the other compounds, mimosine, being a relatively ineffective inhibitor of deoxyhypusine hydroxylation and DNA synthesis in HUVEC, did not cause a significant increase in G1 even at 400 µM after 24 h incubation.

Example 6

This example demonstrates the inhibition of tube formation on Matrigel by ciclopirox, mimosine, deferiprone, deferoxamine, and 2,2'-dipyridyl.

In order to determine the effects of ciclopirox, mimosine, deferiprone, deferoxamine, and 2,2'-dipyridyl on angiogenesis, tube formation on Matrigel in the presence of these compounds was measured, as this system is a model assay of angiogenesis.

The formation of tubes on Matrigel by HUVEC was assessed as described (Kubota et al., *J. Cell. Biol.* 107(4): 1589–1598 (1988) and Ponce, *In Vitro Matrigel Angiogenesis Assays*. Totowa, N.J.: Humana Press Inc., 2000) with minor modifications as follows. Matrigel, 0.3 ml, was added to each well of a 24-well plate. After the Matrigel had gelled, HUVEC ($5 \times 10^4$ cells), trypsinized from an exponentially growing culture, were added to each well in 0.2 ml of supplemented EBM-2. Test compounds were added in duplicate for each concentration and incubated at 37° C., 5% $CO_2$, for 18 h. The medium was aspirated the next day, and the cells were fixed and stained with Diff-Quick Fix and staining solution II (Baxter Scientific Products, McGaw, Ill.).

Alignment of HUVEC was observed 24 h after seeding on Matrigel and tube formation was complete by 18 h. In contrast to the intact enclosure of tubes formed by control HUVEC, those formed in the presence of ciclopirox, 2,2'-dipyridyl, deferiprone and deferoxamine showed disconnected areas. Disruption of tube formation was manifest at 10–20 µM of ciclopirox, and at 100 µM of 2,2-dipyridyl. Modest inhibition was observed at 200 µM of deferiprone and deferoxamine. There was little sign of impairment of tube formation with mimosine even at 400 µM. Thus, the inhibition of tube formation at 18 h of treatment appeared to be consistent with that of proline hydroxylation, confirming the importance of collagen synthesis in tube formation.

Example 7

This example demonstrates the inhibition of chick aortic arch ring sprouting on Matrigel by ciclopirox, mimosine, deferiprone, deferoxamine, and 2,2'-dipyridyl.

Because the chick aortic arch ring sprouting assay is also a model assay of angiogensis, the effects of the compounds on chick aortic arch ring sprouting was determined.

The assay was carried out as described previously for rat aortic rings (Gho et al., 1999), supra) with a slight modification. Briefly, the aortic arches were dissected from 14-day-old chick embryos, cleaned free of unwanted tissue, and cut into 0.8 mm slices. Each ring was transferred into the center of a well of a 24-well plate to which 1.5 µl of Matrigel had just been added. Ten µl of ice-cold Matrigel were added immediately to embed the ring. When the Matrigel was solidified, 500 µl of supplemented EBM-2 were added to each well. After addition of the test compounds in sextuplicate for each concentration, the plates were incubated at 37° C. with 5% $CO_2$, and the degree of sprouting was assessed by a blinded observer after 48 and 72 h.

The inhibitory effects of these compounds were more pronounced in the aortic arch ring sprouting assay after 72 h of incubation. This is an assay that depends not only on HUVEC migration, but also on proliferation. Compared to the continually growing sprouts in the control sample, both density and length of sprouts were markedly reduced in the presence of inhibitors. While ciclopirox was still the most inhibitory, deferoxamine and 2,2'-dipyridyl showed a strong inhibition at 50–100 µM, and deferiprone at 400 µM. Although mimosine was the least effective, a moderate inhibition of sprout growth was observed at 400 µM. The order of inhibition in the ring assay was slightly different from that in tube formation and proline hydroxylation. Deferoxamine, which is a poor inhibitor of proline hydroxylation and tube formation, was nearly as effective as 2,2'-dipyridyl in the ring assay. The strong inhibition by deferoxamine in this more complex assay may result from its strong inhibition of DNA synthesis, and thereby of cell growth.

As these compounds were able to inhibit tube formation on Matrigel (Example 6) and chick aortic arch ring sprouting, it is concluded that these compounds can inhibit the formation of vascular channels.

Example 8

This example demonstrates the inhibition of deoxyhypusine hydroxylase, of DNA synthesis, and of cell cycle progression by ciclopirox in Siha cells.

Siha cells were incubated for 20 hours with increasing concentrations of ciclopirox and then metabolically labeled to determine the ability to inhibit DNA synthesis, as described in Example 4, and the ability to inhibit deoxyhypusine hydroxylation, as described in Example 2. Cell cycle arrest was assessed by flow cytometry, as described in Example 5.

Ciclopirox produced a sharp, dose-dependent inhibition of DNA synthesis in log-phase Siha cells. At 30 µM, ciclopirox increasingly suppressed the hydroxylation of eIF-5A, causing a progressive shift in the ratio between the hydroxylation precursor deoxyhypusine and the hydroxylation product hypusine, amino acid residues unique for eIF-5A. At 30 µM, ciclopirox totally suppressed the deoxyhypusine hydroxylation. Furthermore, ciclopirox at 30 µm caused arrest in late $G_1$, at the $G_1$-S boundary.

Ciclopirox can inhibit cell cycle progression, DNA synthesis, and deoxyhypusine hydroxylation in Siha cells, which are model cells of a non-vascularized intraepithelial neoplasia.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of inhibiting formation of a vascular channel in a tissue with abnormal growth, which method comprises administering to the tissue ciclopirox or a salt thereof at a concentration of about 5 μM or more.

2. The method of claim 1, wherein the ciclopirox or salt thereof is administered topically.

3. The method of claim 2, wherein the tissue is a tissue of a mammal.

4. The method of claim 3, wherein the mammal is a human.

5. The method of claim 2, wherein the tissue is a surface epithelium.

6. The method of claim 2, wherein the tissue is in vivo or ex vivo.

7. The method of claim 2, wherein the method further comprises radiation therapy or chemotherapy with another active agent, and wherein the radiation therapy or the chemotherapy and the ciclopirox or salt thereof are administered either simultaneously or sequentially in either order.

8. The method of claim 7, wherein the ciclopirox or salt thereof is administered before the radiation therapy.

9. The method of claim 2, wherein the method further comprises surgical removal of the abnormal growth, and wherein the ciclopirox or salt thereof is administered prior to the surgical removal of the abnormal growth.

10. A method of inhibiting proliferation of a cell of a non-vascularized intraepithelial neoplasia, which method comprises administering to the tissue ciclopirox or a salt thereof to the cell.

11. The method of claim 10, wherein the ciclopirox or salt thereof is administered topically.

12. The method of claim 11, wherein the intraepithelial neoplasia is from a mammal.

13. The method of claim 12, wherein the mammal is a human.

14. The method of claim 11, wherein the non-vascularized intraepithelial neoplasia is found in an oronasopharnyx, a gastrointestinal tract, or a urogenital tract.

15. The method of claim 14, wherein the non-vascularized intraepithelial neoplasia found in the urogenital tract is found in a cervix, vagina, or a vulva.

16. The method of claim 11, wherein the cell is in vivo or ex vivo.

17. The method of claim 11, wherein the method further comprises radiation therapy and chemotherapy with another active agent, and wherein the radiation therapy, the chemotherapy, and the ciclopirox or salt thereof are administered either simultaneously or sequentially in any order.

18. The method of claim 17, wherein the ciclopirox or salt thereof is administered before the radiation therapy.

19. The method of claim 11, wherein the method further comprises surgical removal of the intraepithelial neoplasia, and wherein the ciclopirox or salt thereof is administered before the surgical removal of the intraepithelial neoplasia.

20. The method of claim 1, wherein the ciclopirox or salt thereof is administered at a concentration of about 10 μM or more.

21. The method of claim 2, wherein the ciclopirox or salt thereof is administered at a concentration of about 10 μM or more.

22. The method of claim 3, wherein the ciclopirox or salt thereof is administered at a concentration of about 10 μM or more.

23. The method of claim 4, wherein the ciclopirox or salt thereof is administered at a concentration of about 10 μM or more.

24. The method of claim 5, wherein the ciclopirox or salt thereof is administered at a concentration of about 10 μM or more.

25. The method of claim 6, wherein the ciclopirox or salt thereof is administered at a concentration of about 10 μM or more.

26. The method of claim 7, wherein the ciclopirox or salt thereof is administered at a concentration of about 10 μM or more.

27. The method of claim 8, wherein the ciclopirox or salt thereof is administered at a concentration of about 10 μM or more.

28. The method of claim 9, wherein the ciclopirox or salt thereof is administered at a concentration of about 10 μM or more.

29. The method of claim 10, wherein the ciclopirox or salt thereof is administered at a concentration of about 5 μM or more.

30. The method of claim 11, wherein the ciclopirox or salt thereof is administered at a concentration of about 5 μM or more.

31. The method of claim 12, wherein the ciclopirox or salt thereof is administered at a concentration of about 5 μM or more.

32. The method of claim 13, wherein the ciclopirox or salt thereof is administered at a concentration of about 5 μM or more.

33. The method of claim 14, wherein the ciclopirox or salt thereof is administered at a concentration of about 5 μM or more.

34. The method of claim 15, wherein the ciclopirox or salt thereof is administered at a concentration of about 5 μM or more.

35. The method of claim 16, wherein the ciclopirox or salt thereof is administered at a concentration of about 5 μM or more.

36. The method of claim 17, wherein the ciclopirox or salt thereof is administered at a concentration of about 5 μM or more.

37. The method of claim 18, wherein the ciclopirox or salt thereof is administered at a concentration of about 5 μM or more.

38. The method of claim 19, wherein the ciclopirox or salt thereof is administered at a concentration of about 5 μM or more.

39. The method of claim 10, wherein the ciclopirox or salt thereof is administered at a concentration of about 10 μM or more.

40. The method of claim 11, wherein the ciclopirox or salt thereof is administered at a concentration of about 10 μM or more.

41. The method of claim 12, wherein the ciclopirox or salt thereof is administered at a concentration of about 10 μM or more.

42. The method of claim 13, wherein the ciclopirox or salt thereof is administered at a concentration of about 10 μM or more.

43. The method of claim 14, wherein the ciclopirox or salt thereof is administered at a concentration of about 10 μM or more.

44. The method of claim 15, wherein the ciclopirox or salt thereof is administered at a concentration of about 10 μM or more.

45. The method of claim 16, wherein the ciclopirox or salt thereof is administered at a concentration of about 10 μM or more.

46. The method of claim 17, wherein the ciclopirox or salt thereof is administered at a concentration of about 10 μM or more.

47. The method of claim 18, wherein the ciclopirox or salt thereof is administered at a concentration of about 10 μM or more.

48. The method of claim 19, wherein the ciclopirox or salt thereof is administered at a concentration of about 10 μM or more.

49. The method of claim 1, wherein the ciclopirox or salt thereof is ciclopirox olamine.

50. The method of claim 2, wherein the ciclopirox or salt thereof is ciclopirox olamine.

51. The method of claim 3, wherein the ciclopirox or salt thereof is ciclopirox olamine.

52. The method of claim 4, wherein the ciclopirox or salt thereof is ciclopirox olamine.

53. The method of claim 5, wherein the ciclopirox or salt thereof is ciclopirox olamine.

54. The method of claim 6, wherein the ciclopirox or salt thereof is ciclopirox olamine.

55. The method of claim 7, wherein the ciclopirox or salt thereof is ciclopirox olamine.

56. The method of claim 8, wherein the ciclopirox or salt thereof is ciclopirox olamine.

57. The method of claim 9, wherein the ciclopirox or salt thereof is ciclopirox olamine.

58. The method of claim 10, wherein the ciclopirox or salt thereof is ciclopirox olamine.

59. The method of claim 11, wherein the ciclopirox or salt thereof is ciclopirox olamine.

60. The method of claim 12, wherein the ciclopirox or salt thereof is ciclopirox olamine.

61. The method of claim 13, wherein the ciclopirox or salt thereof is ciclopirox olamine.

62. The method of claim 14, wherein the ciclopirox or salt thereof is ciclopirox olamine.

63. The method of claim 15, wherein the ciclopirox or salt thereof is ciclopirox olamine.

64. The method of claim 16, wherein the ciclopirox or salt thereof is ciclopirox olamine.

65. The method of claim 17, wherein the ciclopirox or salt thereof is ciclopirox olamine.

66. The method of claim 18, wherein the ciclopirox or salt thereof is ciclopirox olamine.

67. The method of claim 19, wherein the ciclopirox or salt thereof is ciclopirox olamine.

\* \* \* \* \*